United States Patent [19]

Foslien

[11] Patent Number: 4,527,725
[45] Date of Patent: Jul. 9, 1985

[54] STAPLER WITH RETRACTABLE ANVIL
[75] Inventor: Floyd L. Foslien, Stillwater, Minn.
[73] Assignee: Minnesota Mining and Manufacturing Company, Saint Paul, Minn.
[21] Appl. No.: 439,134
[22] Filed: Nov. 4, 1982
[51] Int. Cl.³ .............................................. A61B 17/04
[52] U.S. Cl. ..................... 227/19; 128/334 R; 227/88
[58] Field of Search ............... 227/19, 83, 87, DIG. 1, 227/88; 128/334 R, 334 C; 29/243.56

[56] References Cited

U.S. PATENT DOCUMENTS

| | | |
|---|---|---|
| 1,897,625 | 2/1933 | Svensson . |
| 1,934,104 | 11/1933 | Svensson . |
| 1,945,377 | 1/1934 | Posnack ...................... 227/DIG. 1 |
| 2,185,518 | 1/1940 | Posnack ............................ 227/83 |
| 2,225,054 | 12/1940 | Houwen . |
| 2,265,423 | 12/1941 | Faas . |
| 3,445,912 | 5/1969 | Perlman ........................... 29/207.5 |
| 3,751,961 | 8/1973 | Graf ................................. 227/88 X |
| 3,753,523 | 8/1973 | Perlman .............................. 227/88 |
| 3,873,016 | 3/1975 | Fishbein ...................... 227/DIG. 1 |
| 3,917,145 | 11/1975 | Graf et al. ............................ 227/90 |
| 3,973,709 | 8/1976 | Akopov et al. ..................... 227/19 |
| 4,043,504 | 8/1977 | Hueil et al. ......................... 227/116 |
| 4,202,480 | 5/1980 | Annett ........................ 227/DIG. 1 |
| 4,364,507 | 12/1982 | Savino ................................ 227/83 |

FOREIGN PATENT DOCUMENTS

| | | |
|---|---|---|
| 40683 | 3/1981 | European Pat. Off. . |
| 69557 | 2/1982 | European Pat. Off. . |
| 815658 | 7/1959 | United Kingdom . |
| 189982 | 1/1967 | U.S.S.R. ....................... 227/DIG. 1 |

Primary Examiner—Paul A. Bell
Attorney, Agent, or Firm—Donald M. Sell; James A. Smith; William L. Huebsch

[57] ABSTRACT

A medical stapler adapted to bend a staple closed around an anvil into a generally loop-like shape. The stapler includes a mechanism for retracting the anvil from within the closed staple as a ram that closed the staple moves away from the anvil.

2 Claims, 13 Drawing Figures

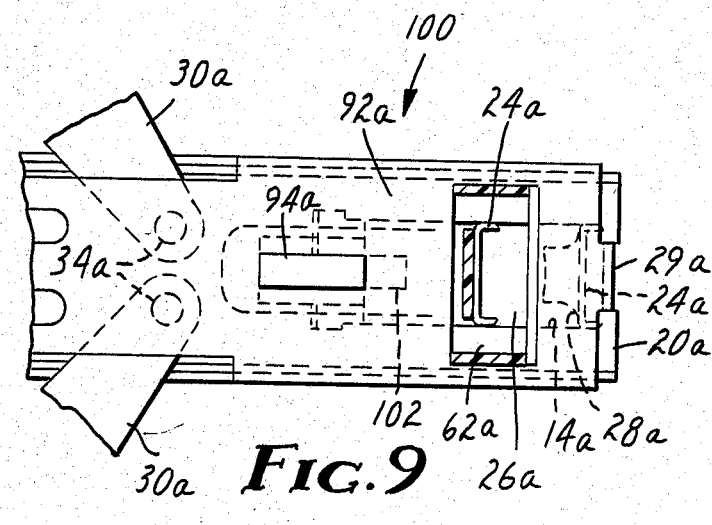
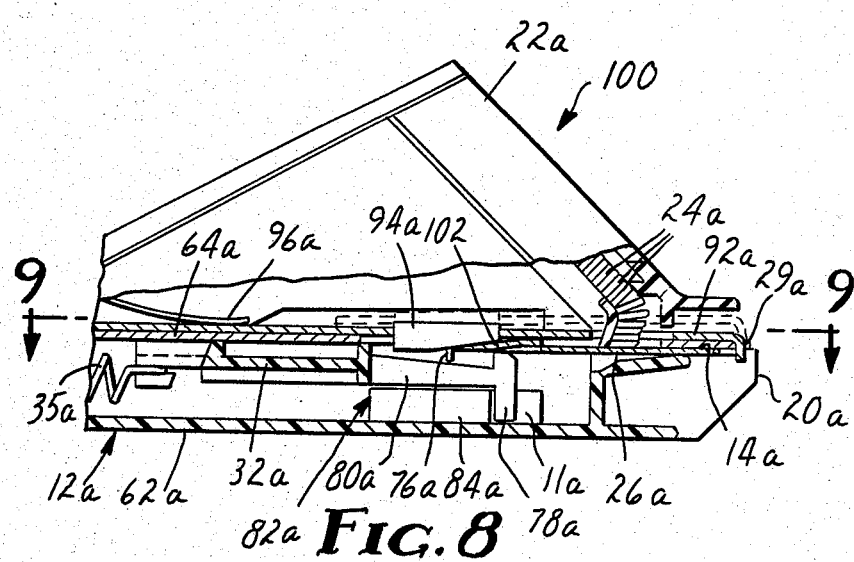

STAPLER WITH RETRACTABLE ANVIL

TECHNICAL FIELD

This application relates to staplers of the type used in the medical field to join disunited tissue by closing a staple around an anvil so that end portions of the staple can enter and join adjacent tissue.

BACKGROUND ART

The art is replete with staplers that close a staple into a closed loop (which loop may be generally rectangular or D-shaped) by bending one or more parts of a central portion of the staple against an anvil so that the staple is closed around the anvil and projecting end portions of the open staple can enter and join living tissues adjacent the anvil (such as portions of disunited skin), and the closed staple which will then hold the tissues together. Illustrative examples of patents describing such staplers include U.S. Pat. Nos. 3,873,016; 4,109,844; 4,202,480; and 4,321,002.

Typically, the anvil in such a stapler is cantilevered, projects past a guide surface for the staple, and has one or more surfaces against which a staple is bent closed, which surfaces may include opposite edge surfaces spaced at a distance corresponding to the distance between spaced parts of the staple to be bent, and/or a contact surface adapted to engage a central portion of the staple to be bent. Means are provided for positioning an open staple at the anvil with the central portion of the staple adjacent the anvil and the end portions of the staple flanking the edge surfaces of the anvil. A ram is mounted on the housing for movement from a load position affording positioning a staple along the guide surface adjacent the anvil, to a formed position so that the ram will bend the staple closed around the anvil and the end portions of the staple can enter adjacent tissues. After the staple is thus closed, the anvil must be pulled from within the closed staple by manually moving the housing of the stapler which is annoying to the user. Also, if this is not first properly done, an attempt to move the housing of the stapler away from the tissue engaged by the staple will pull on the staple and can cause damage to the engaged tissue.

DISCLOSURE OF THE INVENTION

The present invention provides a stapler of the type described above that includes means for retracting an anvil from within a staple bent closed into tissue by the stapler so that no special movement of the housing of the stapler is required by the user before the stapler can be separated from the closed staple.

According to the present invention there is provided a stapler adapted to bend a staple having a central portion and an end portion projecting from each end of its central portion closed into a generally loop-like shape by bending at least one part of its central portion. The stapler comprises a housing having a passageway, and an anvil. Means are provided to mount the anvil on the housing for movement between an engage position projecting across an outlet opening of the passageway, and a retracted position out of the passageway. The anvil has a contact surface disposed generally at right angles to a staple guide surface partially defining the passageway when the anvil is in its engage position, which contact surface is adapted to be engaged by the central portion of the staple. Means are also provided for positioning the staple at the anvil with the central portion of the staple adjacent the contact surface and the end portions of the staple flanking the anvil. A ram is mounted on the housing for movement between a load position affording positioning the staple along the passageway between the ram and anvil when the anvil is in its engage position, and a formed position with the ram more closely adjacent the anvil to bend the staple closed around the anvil. Drive means are provided for moving the ram between its load and formed positions, and cam means are provided between the drive means and the means for mounting the anvil, for moving the anvil to its engage position prior to movement of the ram to its formed position, for maintaining the anvil at its engage position during movement of the ram fully to its formed position and for subsequently moving the anvil to its retracted position during movement of the ram from its formed position to its load position to thus disengage the anvil from the closed staple.

BRIEF DESCRIPTION OF THE DRAWING

The present invention will be further described with reference to the accompanying drawing wherein like numbers refer to like parts in several views, and wherein:

FIG. 8 is a fragmentary sectional side view of a second embodiment of a stapler having a retractable anvil according to the present invention;

FIG. 9 is a fragmentary sectional view taken approximately along line 9—9 of FIG. 8;

DETAILED DESCRIPTION

Figure 1:
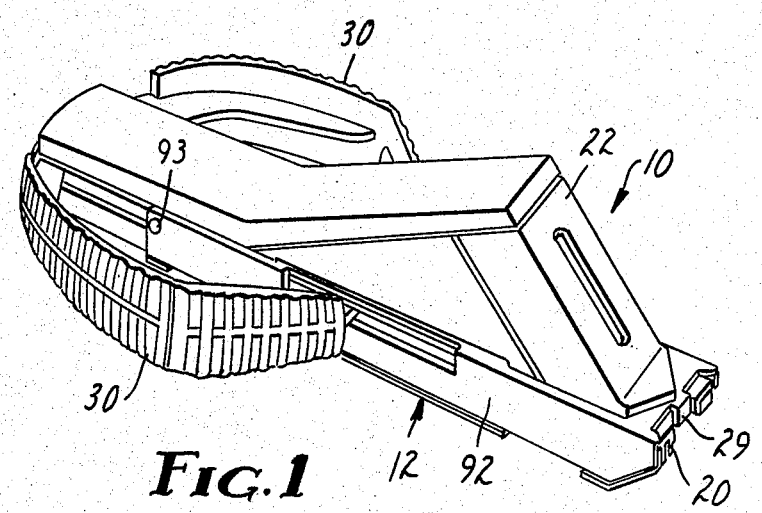
FIG. 1 is a perspective view of a first embodiment of a stapler having a retractable anvil according to the present invention.
Figure 2:
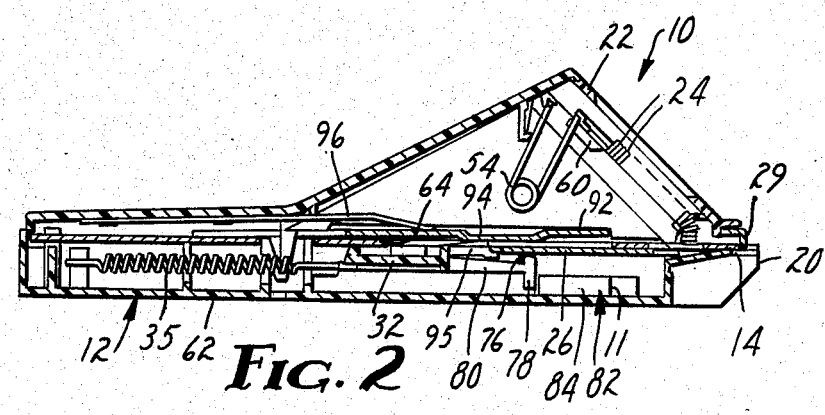
FIG. 2 is a vertical sectional view of the stapler of FIG. 1.

Referring now to FIGS. 1 through 7 of the drawing, there is shown a first embodiment of a stapler, generally designated by the reference number 10, which stapler 10 includes a retractable anvil 29 according to the present invention.

Except for the addition of the retractable anvil 29 and changes in certain other structural aspects which are not central to the present invention (including (1) the use of a staple magazine 22 of the type described in U.S.

patent application No. 147,480, (2) a ram 26 etched on its end as is described in U.S. patent application No. 183,221, and (3) a latching means by which the stapler can be partially activated to hold a staple 24 with end portions of the staple 24 projecting outwardly of the stapler 10 as is described in U.S. patent application No. 234,999; the contents of which applications are all incorporated herein by reference), the stapler 10 has generally the same structure as that of the stapler disclosed in U.S. Pat. No. 4,202,480, the disclosure whereof is also incorporated herein by reference. The parts of the stapler 10 described in this application have been given the same numbers as similar parts of the stapler described in U.S. Pat. No. 4,202,480 to facilitate cross-referencing therebetween.

Like the stapler described in U.S. Pat. No. 4,202,480, the stapler 10 according to the present invention is particularly adapted for use by surgeons to join disunited skin portions by bending a staple 24 closed around the anvil 29 into a loop-like structure so that end portions of the staple 24 will enter and be clenched in skin portions adjacent the anvil 29, after which the anvil 29 is retracted from within the loop-like closed staple 24. In the stapler 10, the anvil 29 is included in an anvil assembly which automatically retracts the anvil 29 from the closed staple 24 without the necessity to move a housing 12 of the stapler 10 for that purpose as is required during use of the stapler described in U.S. Pat. No. 4,202,480.

Briefly the stapler 10 comprises the housing member or housing 12 which has a passageway 14 adapted to guide staples (FIG. 5) extending from an inlet opening at an outlet of the staple magazine 22 to an outlet opening at an end 20 of the housing 12. Means are provided for mounting the anvil 29 for movement between an engage position (FIG. 4) projecting past one side surface partially defining the passageway 14 and centrally across the passageway 14 at the outlet opening, and a retracted position (FIGS. 2 and 3) out of the passageway 14. The anvil 29 has a peripheral contact surface disposed generally at right angles to said side surface along the passageway 14 when the anvil 29 is in its engage position, which peripheral surface is adapted to be engaged by the central portion of the staple 24. The stapler 10 includes means for positioning the staple 24 at the anvil 29 with the central portion of the staple 24 adjacent the contact surface, and end portions of the staple 24 flanking the anvil 29 when the anvil 29 is in its engage position. These means for positioning could be in the form of lugs adapted to hold a single staple against the anvil as is described in U.S. patent application No. 299,068 incorporated herein by reference. In the stapler 10, however, these means comprise (1) the passageway 14 which is adapted to guide staples 24 from the inlet opening to the outlet opening of the passageway 14, (2) the magazine 22 including means in the form of a spring 54 and a follower 60 for biasing a stack of the staples 24 along a track and seriatim into the inlet opening of the passageway 14, and (3) the ram 26 which is mounted on the housing 12 for sliding movement from a load position (FIGS. 2, 3, 5 and 6) with the ram 26 spaced from the inlet opening to afford movement of one of the staples 24 into the passageway 14, along the passageway 14 with the ram 26 pushing the staple 24 adjacent and then into engagement with the anvil 29 when the anvil 29 is in its engage position and to a formed position at which the ram 26 has closed the staple 24 around the anvil 29. Drive means are provided for moving the ram 26 between its load and formed position, and cam means are provided between the drive means and the means for mounting the anvil 29 for moving the anvil 29 to its engage position prior to movement of the ram 26 to its formed position, and for moving the anvil 29 to its retracted position during movement of the ram 26 from its formed position to its load postion.

Figure 3:
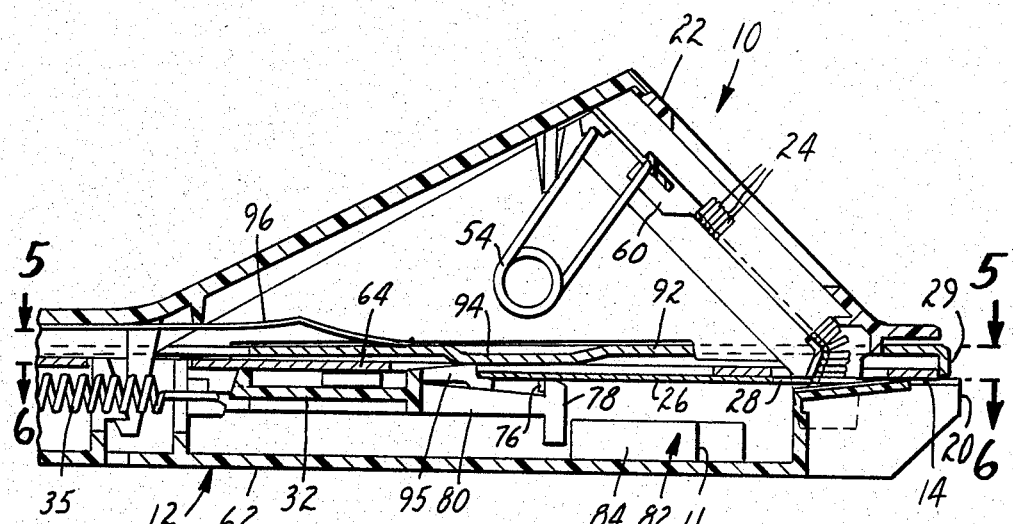
FIG. 3 is an enlarged fragmentary vertical sectional view of the stapler of FIG. 1 showing a ram in a load position and the anvil in a retracted position.
Figure 4:
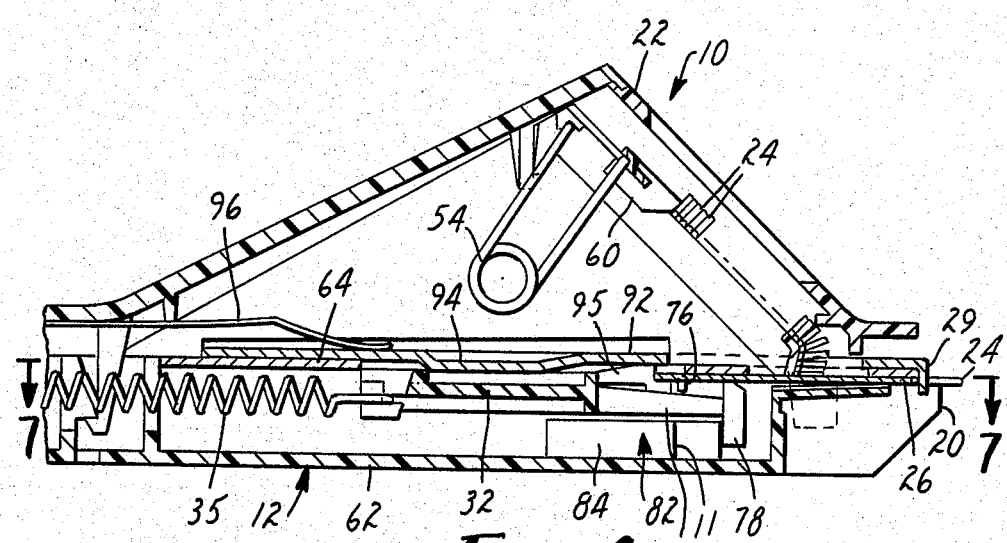
FIG. 4 is a sectional view similar to FIG. 3 but which shows the ram in a formed position and the anvil in an engage position.
Figure 7:
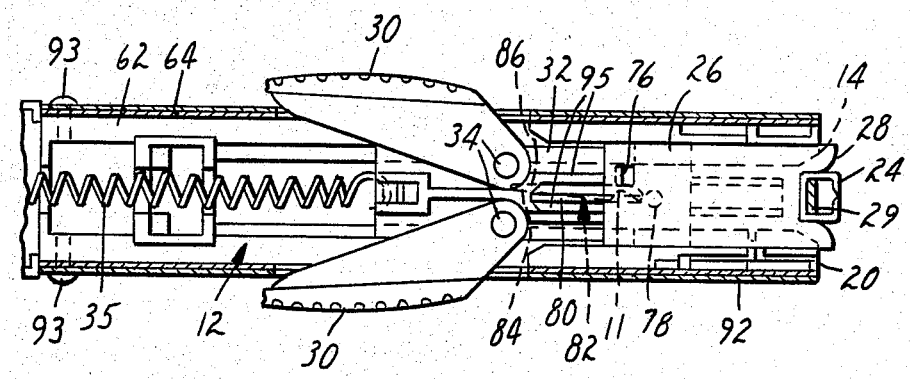
Figure 10:
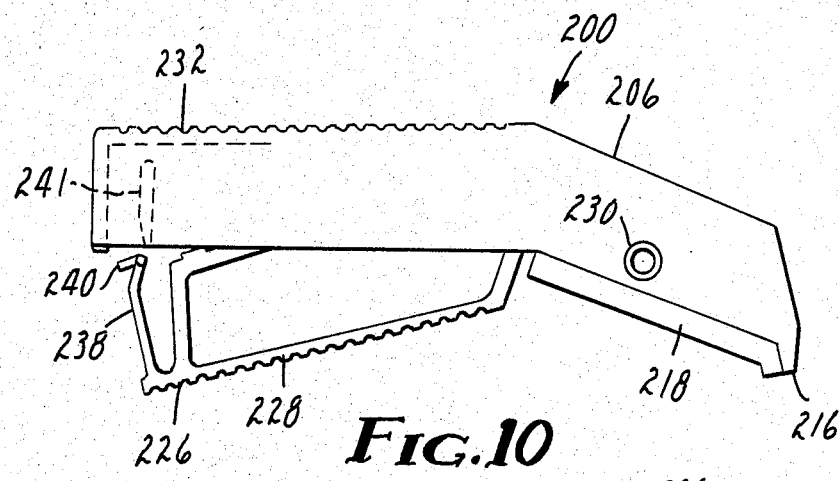
FIG. 10 is a side view of a third embodiment of a stapler having a retractable anvil according to the present invention.

The drive means are manually activatable by pressing opposed flexible handle members 30 together to propel a drive member 32 (pivotably coupled to adjacent ends of the handle members 30 at pins 34) along the passageway 14 from an initial position (FIGS. 2, 3, 5 and 6) to an extended position (FIGS. 4 and 7) to correspondingly move the ram 26 from its load position (FIGS. 3 and 6) to its formed position (FIGS. 4 and 7). The handle members 30 are resiliently flexible so that they will tend to return to their original shape when pressure on them is released and a return coil spring 35 is coupled between the housing 12 and the drive member 32 so that the drive member 32 is biased to its initial position. The drive member 32 can abut the ram 26 to push the ram 26 from its load position (FIGS. 3 and 6) to its formed position (FIGS. 4 and 7), but will not return the ram 26 toward its load position if the drive means is deactivated by removing pressure from the handle members 30 before the ram 26 is pushed fully to its formed position so that the ram 26 then prevents a second staple 24 from entering the passageway 14 before the staple 24 already in the passageway 14 is closed and ejected. Means are provided for coupling the drive member 32 to the ram 26 when the handle members 30 have been pressed together sufficiently to move the ram 26 fully to its formed position, however, so that the ram 26 will subsequently be returned to its load position under the influence of the biasing provided by the spring 35 and the resilience of the handle members 30 when pressure on the handle members 30 is released.

The means for coupling the drive member 32 and the ram 26 when the drive mechanism has positioned the ram in its formed position (FIG. 7) comprises a first lug 76 projecting from one side of the ram 26 and a second lug 78 supported on the drive member 32 for movement transverse of the passageway 14 by a flexible, resilient blade 80 having its end opposite the second lug 78 fixed on the drive member 32. Also included is an elongate cam 82 which is a part of a molded portion 62 of the housing 12, which cam 82 projects centrally into the passageway 14 and provides means (1) for maintaining the second lug 78 in a spaced position out of engagement with the first lug 76 on the ram 26 during movement of the drive member 32 to move the ram 26 from its load toward its formed position; (2) for moving the second lug 78 to an engage position with the lugs 76 and 78 in engagement with each other after the drive member 32 has pushed the ram 26 fully to its formed position; and (3) for subsequently maintaining the second lug 78 in its engaged position during movement of the drive member 32 and ram 26 back to the load position of the ram 26.

Additionally, the second lug 78, the flexible blade 80 on which the second lug 78 is mounted, the drive member 32 on which the blade 80 is mounted, and the cam 82 with its notch 11 are included in latching means which stops movement of the ram 26 away from the anvil 29 at the predetermined intermediate position of the ram 26 between its load and formed positions only during movement of the ram 26 from its load position toward its formed position, at which intermediate position the ram 26 presses the staple 24 in the passageway 14 against the anvil 29 and parallel end portions of the staple 24 project from the outlet opening 18 of the stapler on opposite sides of the anvil 29 (not shown; see U.S. patent application No. 234,999).

The second lug 78 has an end portion projecting from the end of the blade 80 away from the molded portion 62 of the housing 12, which end portion with the blade 80 can pass along an opening in the housing 12 between the ram 26 and the molded portion 62 of the housing 12 but will engage with the first lug 76. The second lug 78 also has an end portion projecting toward the molded portion 62 of the housing 12 to a position where it will engage surfaces of the cam 82. Upon manual activation of the stapler 10, the second lug 78 is positioned by the blade 80 so that it will engage an adjacent first end surface of the cam 82 and will be cammed by that end surface onto a first side surface 84 of the cam 82 out of engagement with the first lug 76 on the ram 26 as the drive member 32 pushes the ram 26 toward its formed position, thereby affording separation of the drive member 32 and the ram 26 if pressure on the handle members 30 is released before the ram 26 is pushed to an intermediate position. Subsequently, when the drive member 32 has pushed the ram 26 to the intermediate position, the second lug 78 will move into a notch 11 in the cam 82 under the biasing influence of the blade 80. The notch 11 is generally C-shaped and aligned so that the lug 78 cannot move out of the notch 11 as a result of forces tending to move the lug 78 away from the end 20 of the stapler to latch the drive member 32 and thereby the ram 26 in its intermediate position if forces tending to move the drive member 32 are discontinued at that point. The shape of the notch 11 will, however, allow movement of the second lug 78 out of the notch 11 upon further activation of the drive member 32 to move the ram 26 toward its formed position. Upon such further activation, just before the drive member 32 has pushed the ram 26 fully to its formed position, the second lug 78 moves off the end of the cam 82 and the resilience of the blade 80 positions the second lug 78 adjacent a second end surface of the cam 82 (FIG. 7). Upon subsequent movement of the drive member 32 back toward its initial position, when manual pressure on the handle members 30 is released, the second lug 78 will engage the cam 82 on its second end surface which will cam the second lug 78 onto a second side surface 86 of the cam 82 and engage the second lug 78 with the first lug 76. The ram 26 will subsequently be pulled back to its load position via engagement of the lugs 78 and 76 as the drive member 32 is returned to its start position under the biasing influence of the spring 35 and the resilient handle members 30.

The means for mounting the anvil 29 and the cam means which interact to retract the anvil 29 from the closed staple 24 are best seen in FIGS. 3 and 4. The anvil 29 is part of a metal anvil support bracket 92 which overlays a portion of the top cover 64 of the housing 12, has a distal end on which the anvil 29 is formed and an opposite end mounted on the housing 12 by a pair of coaxial pins 93 for pivotal movement to move the anvil 29 between its engage and retracted positions. The cam means include projecting cam members or portions 94 and 95 of the anvil support bracket 92 and drive member 32 respectively adapted for sliding engagement with each other, and a spring 96 fixed at one end to the housing 12 which has an opposite end that biases the anvil support bracket 92 toward a position with the anvil 29 in its engage position. The cam members 94 and 95 are shaped to bear against each other and position the anvil 29 in its retracted position when the drive member 32 is in its initial position (FIG. 3), to move out of engagement with each other so that the spring 96 will move the anvil 29 to its engage position as the drive member 32 moves to its extended position and thereby moves the ram 26 to its formed position (FIG. 4) to close the staple 24; and to then move back into engagement to move the anvil 29 from its engaged to its retracted position as the drive member 32 is returned to its initial position and thereby returns the ram 26 to its load position via engagement of the lugs 76 and 78. Such movement of the anvil 29 to its retracted position causes the anvil 29 to be pulled from within the closed staple 24. The closed staple 24 does not tend to move with the anvil 29 because the side of the central portion of the closed staple 24 toward which the anvil 29 moves as it is retracted lays against the side surface of the top cover 64 that partially defines the passageway 14.

Figure 5:
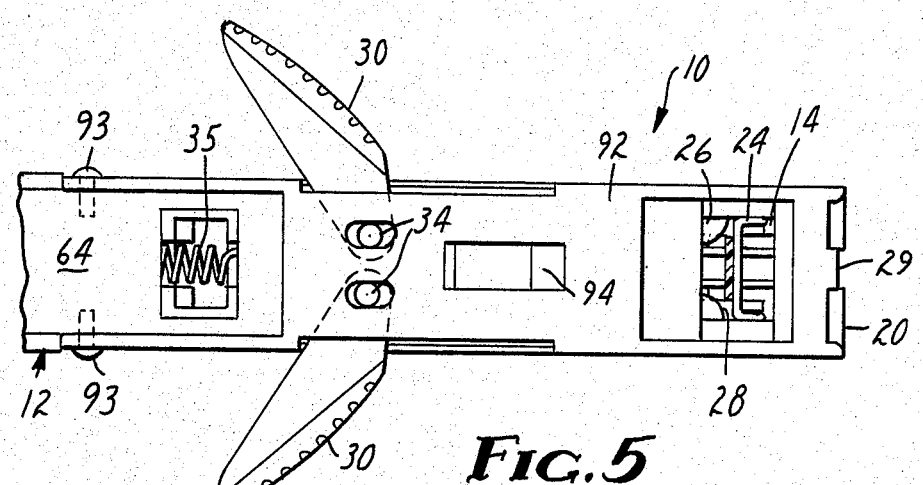
FIG. 5 is a fragmentary sectional view taken approximately along line 5—5 of FIG. 3.
Figure 6:
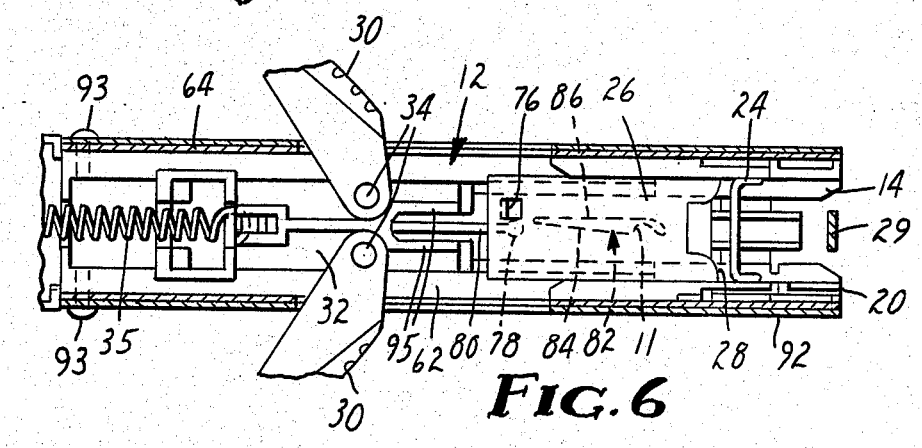
FIGS. 6 and 7 are fragmentary sectional views taken approximately along lines 6—6 of FIG. 3 and line 7—7 of FIG. 4 respectively.

As can best be seen in FIGS. 1 and 5, the anvil support bracket 92 extends about three-quarters the length of the housing 12 so that the distance between the anvil 29 and the pins 93 that provide the pivot axis for the anvil support bracket 92 is quite long (e.g., about $3\frac{5}{8}$ inches or about 9.1 centimeters) which causes the anvil 29 to move at about a right angle to the passageway 14 between its engage and retracted positions. Also, the pins 93 that provide the pivot axis for the anvil support bracket 93 are generally in alignment with the passageway 14 so that the force exerted by the ram 26 to close a staple 24 around the anvil 29 will have little tendency to move the anvil 29 toward its spaced position.

Operation

To operate the stapler 10, a user (such as a surgeon) grasps the stapler 10 around the handle members 30 and squeezes the handle members 30 together to move the drive member 32 away from its initial position (FIGS. 3 and 6) into engagement with the ram 26, and push the ram 26 from its load position (FIGS. 3 and 6) toward its eject position (FIGS. 4 and 7). As the drive member 32 moves into engagement with the ram 26, the second lug 78 carried on the flexible blade 80 will engage the first end surface of the cam 82 which will cam the second lug 78 onto the first side surface 84 of the cam 82 out of alignment with the first lug 76 on the ram 26, and the drive member 32 will push the ram 26 along the passageway 14 into engagement with a single staple 24 at the inlet opening of the passageway 14 to move it along the passageway 14. Also, the cam member 95 on the drive member 32 will move out of engagement with the cam member 94 on the anvil support bracket 92, which allows the spring 96 to move the anvil support bracket 92 and position the anvil 29 in its engage position across the passageway 14. When the ram 26 has thus moved the staple 24 so that it is pressed against the anvil 29 and the parallel end portions of the staple 24 protrude from the outlet opening 18, the second lug 78 will drop into the notch 11. If the user now releases the pressure he is applying to the handle members 30, the drive member 32 and ram 26 will stay in this intermediate position at which the user can engage the staple ends with material to be stapled such as tissue edges to bring them together for better approximation before finally squeezing the handles 30 to drive the ram 26 to its formed position (FIGS. 4 and 7) at which the staple 24 is closed in the tissue. The user can then hold the handles 30 together if desired to hold the closed staple 24 against the anvil 29 at the end of the stapler 10 and thus hold or move the stapled tissue as desired. When the user allows the handle members 30 to return to their normal position under the influence of the spring 35 and resilient handle members 30, however, the cam member 95 on the drive member 32 will again move into engagement with the cam member 94 on the anvil support bracket 92 and cause it to move in opposition to the spring 96 so that the anvil 29 will move from within the closed staple 24 without the need to move the housing 12 of the stapler 10. Also the second lug 78 will move along the second end surface and second side surface 86 of the cam 82 which will move it into engagement with the first lug 76 on the ram 26 so that via the engaged lugs 76 and 78 the ram 26 will be pulled to its load position as the drive member 32 is returned to its initial position.

Second Embodiment

Referring now to FIGS. 8 and 9 there is shown a second embodiment of a stapler 100 which also includes a retractable anvil 29a according to the present invention.

The stapler 100 is quite similar to the stapler 10, and corresponding parts have been given corresponding reference numerals except for the addition of the suffix "a". The stapler 100 is different from the stapler 10 primarily in that cam members 102 that interact with cam members 94a on an anvil support bracket 92a to cause movement of the anvil 29a are mounted on a ram 26a rather than on a drive member 32a.

Like the stapler 10, the stapler 100 has a housing 12a having a passageway 14a adapted to guide a staple 24a extending from an inlet opening at an outlet of a staple magazine 22a to an outlet opening at an end 20a of the housing 12a; a magazine 22a including a spring and follower (not shown) that bias staples 24a into the inlet opening of the passageway 14a; the ram 26a which can be driven along the passageway 14a via handle members 30a and a drive member 32a against the bias of a return coil spring 35a to close a staple 24a against the anvil 29a on the follower 60a; and lugs 76a and 78a on the ram 26a and a blade 80a supported on the follower 60a respectively which move between a molded portion 62a and a top cover 64a of the housing 12a and interact with a cam 82a on the housing 12a to interconnect and release the ram 26a and drive member 32a, all in the manner described above with respect to the stapler 10.

Also included is the metal anvil support bracket 92a which overlays a portion of the top cover 64a of the housing 12a, has a distal end on which the anvil 29a is formed, and an opposite end mounted on the housing 12a by a pair of coaxial pins (not shown) for pivotal movement to move the anvil 29a between its engage and retracted positions. The cam means include the cam members or portions 102 and 94a of the anvil support bracket 92a and the ram 26a respectively, which cam members 102 and 94a are adapted for sliding engagement with each other, and a spring 96a fixed at one end to the housing 12a which has an opposite end that biases the anvil support bracket 92a toward a position with the anvil 29a in its engage position. The cam members 94a and 102 are shaped to bear against each other and position the anvil 29a in its retracted position when the ram 26a is in its load position, to move out of engagement with each other so that the spring 96a will move the anvil 29a to its engage position as the ram 26a is moved to its formed position via the drive member 32a and to then move back into engagement to move the anvil 29a from its engage to its retracted position as the ram 26a is returned to its load position via engagement of the lugs 76a and 78a between the drive member 32a and ram 26a.

Third Embodiment

Referring now to FIGS. 10 through 13 of the drawing, there is shown a third embodiment of a stapler generally designated by the reference number 200, which stapler 200 also includes a retractable anvil 202 according to the present invention.

Except for the addition of the retractable anvil 202, the stapler 10 has essentially the same structure as the stapler sold by the Davis and Geck Division of American Cyanamid, Danbury, Conn. under the trademark "Appose", and which is described in European patent application No. 40,683 (incorporated herein by reference).

Like the stapler 10, the stapler 200 according to the present invention is adapted for use by surgeons to join disunited skin portions by bending a staple 204 closed around the anvil 202 into a loop-like structure so that ends of the staple 204 will enter and be clenched in skin portions adjacent the anvil 202, after which the anvil 202 is retracted from within the loop-like closed staple 204. In the stapler 200, the anvil 202 is automatically retracted from within the closed staple 204 without the necessity to move a housing 206 of the stapler 200 for that purpose as is required during use of the stapler as currently commercially available from Davis and Geck.

Briefly, the stapler 200 comprises a housing member 206 which is elongate and has at one end a passageway 208 adapted to guide staples (FIGS. 10 and 11) extending from an inlet opening at an outlet of a staple magazine 218 to an outlet opening at an end 216 of the housing 206. Means are provided for mounting the anvil 202 for movement between an engage position (FIG. 12) projecting past a side surface partially defining the passageway 208 centrally across the passageway 208 at the outlet opening, and a retracted position (FIG. 11) out of the passageway 208. The anvil 202 has a peripheral contact surface disposed generally at right angles to said surface along the passageway 208 when the anvil 202 is in its engage position, which peripheral surface is adapted to be engaged by the central portion of the staple 204. The stapler 200 includes means for positioning the staple 204 at the anvil 202 with the central portion of the staple 204 adjacent the contact surface, and end portions of the staple 204 flanking the anvil 202 when the anvil 202 is in its engage position, which means comprises the passageway 208 which is adapted to guide staples 204 from the inlet opening to the outlet opening of the passageway 208; the magazine 214 which includes means in the form of a spring 220 and a follower 222 for biasing a stack of the staples 204 along a track and seriatim into the inlet opening of the passageway 208, and a ram 224 which is mounted on the housing 206 for sliding movement from a load position (FIG. 11) with the ram 224 spaced from the inlet opening of the passageway 208 to afford movement of one of the staples 204 into the passageway 208, along the passageway 208 with the ram 224 pushing the staple 204 adjacent and then into engagement with the anvil 202 when the anvil 202 is in its engage position and to a formed position at which the ram 224 has closed the staple 204 around the anvil 202.

Drive means are provided for moving the ram 224 between its load and formed positions, and cam means are provided between the drive means and the means for mounting the anvil 202 for moving the anvil 202 to its engage position prior to movement of the ram 224 to its formed position, and for moving the anvil 202 to its retracted position during movement of the ram 224 from its formed position to its load position.

The drive means for the stapler 200 is activatable by manually squeezing together a handle end 226 of an activating member 228 pivotably mounted on the housing member 206 at a pin 230 and a handle end 232 of the housing member 206 opposite the passageway 208 so that the housing and activating members 206 and 228 are pliers-like members that act in the manner of a pliers and an end portion 234 of the member 228 opposite its handle end 226 is operably connected to and moves the ram 224 from its load position (FIG. 11) to its formed position (FIG. 12) against the bias of a coil spring 236 which biases the ram 224 toward its load position.

The stapler 200 also includes means for preventing a second staple 204 from entering the passageway 208 before a staple 204 already in the passageway 208 is formed and ejected in the event the drive means is deactivated by removing pressure from the handle ends 226 and 232 before the ram 224 is pushed entirely to its formed position. The ram 224 has a length adapted so that portions of the ram 224 will always be positioned adjacent the inlet opening of the passageway 208 during movement of the ram 224 from its load to its formed position to prevent movement of the adjacent staple 204 in the magazine 214 into the passageway 208 through the inlet opening until a staple 204 already in the passageway 208 is closed and ejected. A flexible blade 238 is cantilevered from the handle member 228 and has a resiliently compressible generally V-shaped head 240 at its end opposite the handle end portion 226 that will move along a track 241 within the handle end 232 of the member 206 while being compressed and directed so that it can move in only one direction to prevent separation of the handle ends 226 and 232 and thereby movement of the ram 224 away from the anvil 202 while the ram 224 is being moved from its load position toward its formed position. When the ram 224 reaches its formed position, the head 240 will move out of an end of the track 241, and because the track 241 is disposed to cause bending of the blade 238, the head 240 will be carried by the blade 238 as it returns to its normal shape to a position with the head 240 spaced from the track 241 so that the head 240 can freely move within the housing member 206 and the handle ends 226 and 232 can separate under the influence of the spring 236.

Figure 13:
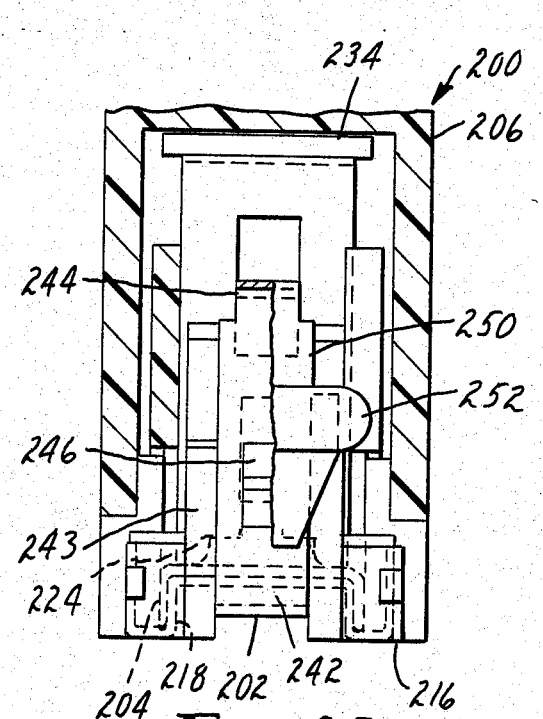
FIG. 13 is an enlarged fragmentary front sectional view of the stapler of FIG. 10.
Figures 11, 12:
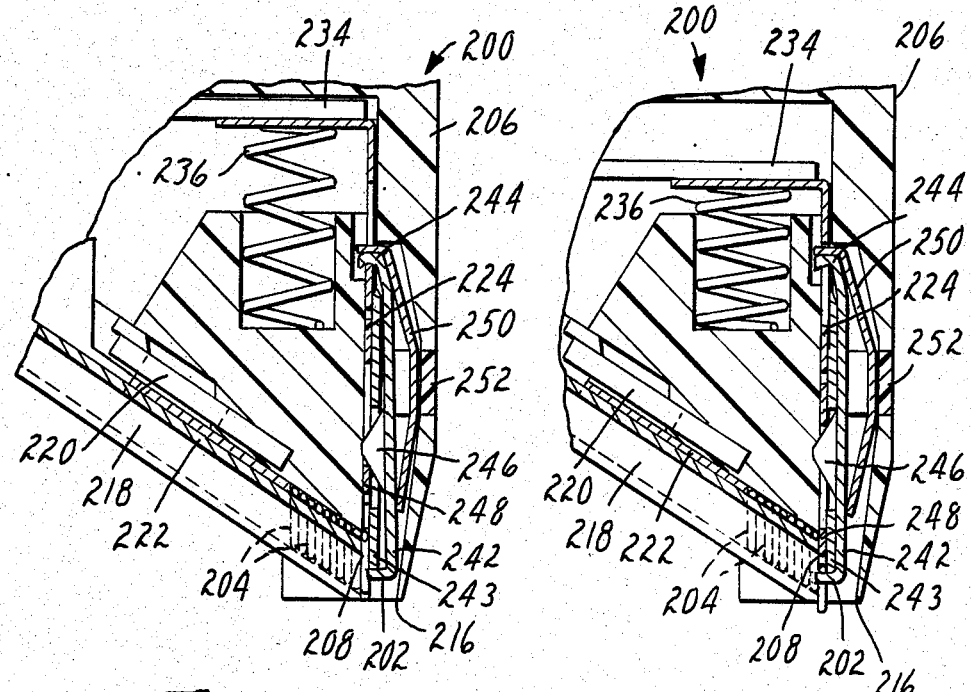
FIG. 11 is an enlarged fragmentary side sectional view of the stapler of FIG. 10 showing a ram in a load position and the anvil in a retracted position.
FIG. 12 is a sectional view similar to FIG. 11 but which shows the ram in a formed position and the anvil in an engage position.

The means for mounting the anvil 202 and the cam means which operates to retract the anvil 202 from the closed staple 204 are best seen in FIGS. 11, 12 and 13. The anvil 202 is part of a metal anvil support bracket 242 which overlays a plate 243 included in the housing member 206 that defines one side of the passageway 208. The support bracket 242 has the anvil 202 formed on one end and a hook 244 on its opposite end, which hook 244 projects through slots in both the plate 243 and the ram 224 and is engaged over an edge of the plate 243 that affords pivotal movement of the support bracket 242 to move the anvil 202 between its engage and retracted positions. The cam means include cam members or portions 246 and 248 of the anvil support bracket 242 and ram 224 respectively adapted for sliding engagement with each other and a leaf spring 250 retained between the support bracket 242 and a bar 252 included in the housing 206. The spring 250 has one end bent so that it biases the hook 244 against the edge of the plate 243 over which it is engaged, and an opposite end that biases the anvil support bracket 242 toward a portion with the anvil 202 in its engage position. The cam members 246 and 248 are shaped to bear against each other and position the anvil 202 in its retracted position when the ram 224 is in its load position (FIG. 11), to move out of engagement with each other so that the spring 250 will move the cam members 248 into openings in the ram 224 and will move the anvil 202 to its engage position as the ram 224 moves from its load to its formed position (FIG. 12) to close the staple 204; and to then move back into engagement to move the anvil 202 from its engage to its retracted position as the ram 224 is returned from its formed to its load position. Such movement of the anvil 202 to its retracted position causes the anvil 202 to be pulled from within the closed staple 204. The closed staple 204 does not tend to move with the anvil 202 because the side of the central portion of the closed staple 204 toward which the anvil 202 moves as it is retracted lays against the side surface of the plate 243 that partially defines the passageway 208.

As can best be seen in FIGS. 11 and 12, the anvil support bracket 242 extends for at least a moderate distance along the length of the plate 243 so that the distance between the anvil 202 and the hook 244 that provides the pivot axis for the anvil support bracket 242 (e.g., about ¾ inch or 1.9 centimeters) causes the anvil 202 to move at approximately a right angle to the passageway 208 between its engage and retracted positions. Also, the hook 244 that provides the pivot axis for the anvil support bracket 242 is generally in alignment with the passageway 208 so that the force exerted by the ram 224 to close a staple 204 around the anvil 202 will have little tendency to move the anvil 202 toward its retracted position.

Operation

To operate the stapler 200, a user (such as a surgeon) grasps the stapler 200 around the handle ends 226 and 232 of the housing and activating members 206 and 228 and squeezes them together to push the ram 224 from its load position (FIG. 11) toward its eject position (FIG. 12) and into engagement with a single staple 204 positioned by the staple magazine 214 at the inlet opening of the passageway to move the staple 204 along the passageway 208. This causes the cam member 248 on the ram 224 to move out of engagement with the cam member 246 on the anvil support bracket 242, which allows the spring 250 to move the anvil support bracket 242 and position the anvil 202 in its engage position across the passageway 208. Such squeezing of the handle ends 226 and 232 will drive the ram 224 to its formed position (FIG. 12) at which the staple 204 is closed around the anvil 202. The user can then hold the handle ends 226 and 232 together if desired to hold the closed staple 204 against the anvil 202 at the end of the stapler 200 and thus hold or move the stapled tissue as desired. When the user allows the handle ends 226 and 232 to return to their normal position under the influence of the spring 236, however, the cam member 248 on the ram 224 will again move into engagement with the cam member 246 on the anvil support bracket 242 and cause it to move in opposition to the spring 250 so that the anvil 202 will move from within the closed staple 204 without the need to manually move the housing member 206 of the stapler 200.

I claim:

1. A stapler adapted to bend a staple having a central portion and an end portion projecting from each end of said central portion closed into a generally loop-like shape by bending at least one part of said central portion, said stapler comprising:

a housing having a passageway with an outlet opening;

an anvil having a contact surface adapted to be engaged by the central portion of a said staple;

means mounting said anvil on said housing for movement between an engage position projecting across said passageway at said outlet opening, and a retracted position out of said passageway;

means for positioning a said staple at said anvil with the central portion of the staple adjacent said contact surface and the end portions of said staple flanking said anvil;

a ram mounted on said housing for movement between a load position affording positioning a said staple along said passageway between said ram and anvil when said anvil is in said engage position, and a formed position with said ram more closely adjacent said anvil to bend the staple closed around said anvil;

drive means for moving said ram between said load and formed positions; and cam means between said drive means and said means for mounting said anvil for moving said anvil to said engage position prior to movement of said ram to said formed position, for maintaining said anvil at said engage position during movement of said ram fully to said formed position, and for subsequently moving said anvil to said retracted position during movement of said ram from said formed position to said load position;

said housing including a surface positioned to support the central portion of a said staple closed around said anvil to prevent movement of the closed staple relative to said housing during movement of said anvil from said engage to said retracted position.

2. A stapler according to claim 1 wherein said means mounting said anvil on said housing comprises an anvil support bracket having said anvil fixed adjacent one end and being mounted on said housing for pivotal movement to move said anvil between said engaged and retracted positions about an axis generally aligned with said passageway.

* * * * *